United States Patent
Rejdak

(10) Patent No.: US 12,171,775 B2
(45) Date of Patent: Dec. 24, 2024

(54) USE OF CLADRIBINE FOR TREATING AUTOIMMUNE NEUROMUSCULAR DISEASE

(71) Applicant: Chord Therapeutics SA, Geneva (CH)

(72) Inventor: Konrad Rejdak, Lublin (PL)

(73) Assignee: Chord Therapeutics SA, Geneva (CH)

( * ) Notice: Subject to any disclaimer, the term of this patent is extended or adjusted under 35 U.S.C. 154(b) by 0 days.

(21) Appl. No.: 16/632,245

(22) PCT Filed: Jun. 28, 2018

(86) PCT No.: PCT/GB2018/051801
§ 371 (c)(1),
(2) Date: Jan. 17, 2020

(87) PCT Pub. No.: WO2019/016505
PCT Pub. Date: Jan. 24, 2019

(65) Prior Publication Data
US 2020/0163986 A1 May 28, 2020

(30) Foreign Application Priority Data
Jul. 21, 2017 (GB) ..................... 1711800

(51) Int. Cl.
*A61K 31/7076* (2006.01)
*A61K 9/00* (2006.01)
*A61P 21/04* (2006.01)

(52) U.S. Cl.
CPC ........ *A61K 31/7076* (2013.01); *A61K 9/0019* (2013.01); *A61P 21/04* (2018.01)

(58) Field of Classification Search
CPC .... A61K 31/7076; A61K 9/0019; A61P 21/04
USPC ........................................................ 514/56
See application file for complete search history.

(56) References Cited

U.S. PATENT DOCUMENTS 7,713,947 B2 * 5/2010 De Luca ............... A61P 25/00
424/85.6

FOREIGN PATENT DOCUMENTS

| WO | WO 01/07054 A1 * | 2/2001 | ......... A61K 31/7076 |
| WO | WO-2004/041195 A2 | 5/2004 | |
| WO | WO2004/0491195 A2 * | 5/2004 | ......... A61K 31/7076 |
| WO | WO-2007/135172 A2 | 11/2007 | |

OTHER PUBLICATIONS

The Merck Manual, 1992, 16th Edn., p. 1489.*
Guptill et al, Neurotherapeutics, 2016, 13, 118-131.*
Costello et al , J. Neuroscience Nursing, 2008, 40, 275-280.*
International Application No. PCT/GB2018/051801, Search Report and Written Opinion, mailed Aug. 30, 2018, 9 pgs.
United Kingdom Application No. GB1711800.1, Search Report, Apr. 17, 2018, 2 pgs.
Chitnis, T., "The Role of CD4 T Cells in the Pathogenesis of Multiple Sclerosis", International Review of Neurobiology, 79, (2007), 43-62.
Costello, K., et al., "Cladribine Tablets' Potential in Multiple Sclerosis Treatment", Journal of Neuroscience Nursing, 40, (Oct. 2008), 275-280.
Guptill, J. T., et al., "Current Treatment, Emerging Translational Therapies, and New Therapeutic Targets for Autoimmune Myasthenia Gravis", Neurotherapeutics, 13, (2016), 118-131.
Kopadze, T., et al., "Cladribine impedes in vitro migration of mononuclear cells: a possible implication for treating multiple sclerosis", European Journal of Neurology, 16, (2009), 409-412.
Laugel, B., et al., "Cladribine inhibits cytokine secretion by T cells independently of deoxycytidine kinase activity", Journal of Neuroimmunology,, (2011), 52-57.
Leist, T.P., et al., "Cladibrine: Mode of Action and Implication for Treatment of Multiple Sclerosis", Clin. Neuropharm., 34, (2011), 28-35.
Rezania, K., et al., "Myasthenia gravis, an autoimmune manifestation of lymphoma and lymphoproliferative disorders: case reports and review of literature", Leukemia & Lymphoma, 53, (Mar. 2012), 371-380.
Schirmer, M., et al., "The Safety Profile of Low-dose Cladribine in Refractory Rheumatoid Arthritis", Scandinavian Journal of Rheumatology, 26:5, 376-379, (1997), 376-379.

* cited by examiner

Primary Examiner — Ganapathy Krishnan
(74) Attorney, Agent, or Firm — Schwegman Lundberg & Woessner, P.A.

(57) ABSTRACT

The present invention relates to the use of 2-chloro-2'-deoxyadenosine, hereinafter referred to as cladribine, or a pharmaceutically acceptable salt thereof, for treating or ameliorating an autoimmune, neuromuscular disorder, e.g. the autoimmune neuromuscular disorder myasthenia gravis (MG).

6 Claims, No Drawings

USE OF CLADRIBINE FOR TREATING AUTOIMMUNE NEUROMUSCULAR DISEASE

This application is a U.S. National Stage Filing under 35 U.S.C. 371 from International Application No. PCT/GB2018/051801, filed on Jun. 28, 2018, and published as WO 2019/016505 A1 on Jan. 24, 2019, which claims the benefit of priority to United Kingdom Patent Application No. 1711800.1, filed on Jul. 21, 2017, each of which is incorporated by reference herein in its entirety.

FIELD OF THE INVENTION

The present invention relates to the use of 2-chloro-2'-deoxyadenosine, hereinafter referred to as cladribine, or a pharmaceutically acceptable salt thereof, for treating or ameliorating an autoimmune, neuromuscular disorder, e.g. the autoimmune neuromuscular disorder myasthenia gravis, hereinafter referred to as MG.

BACKGROUND TO THE INVENTION

Autoimmune diseases are a large family of disorders in which the activity of elements of the immune system, which protect against illness by attacking or suppressing infections or malignancies, are aberrantly activated against some of the body's own normal proteins or other structures. In autoimmune neuromuscular diseases antibodies are detected that bind to targets on nerves or muscle and lead to symptoms that range from moderate to severe and can include weakness in specific muscles or more generally, fatigue, being wheelchair bound or bedridden, or even death. These acquired antibody-mediated forms include autoimmune and neonatal myasthenia gravis, Lambert-Eaton myasthenic syndrome, and neuromyotonia. Variability in disease presentation is common and severity can vary markedly between patients with the same disorder.

MG is a rare autoimmune neuromuscular disorder which forms the largest disease group of neuromuscular junction disorders and is caused by pathogenic autoantibodies to components of the postsynaptic muscle endplate. It has a prevalence that is estimated to be 78 per 1,000,000 of the population worldwide (Carr A. et al.; BMC Neurol 18:46 (2010)), resulting in a calculated 65,000 patients in the US and Europe combined. A number of reports suggest that the prevalence is increasing especially in the elderly, in a manner greater than can be accounted for by an ageing population. The age of onset can vary from adolescence or even childhood, to late adulthood with peak incidence occurring around 30 years of age. There is a marked female to male preponderance in younger onset cases, in common with many autoimmune disorders. No strong external causative factors such as infection or diet have been reported.

The most common symptom is muscle weakness, which can vary over time and from one muscle group to another in the same individual. Commonly-affected muscle groups include eye muscles, muscles of the mouth and throat, limb and trunk muscles. In about 20% of cases eye and eyelid muscles only are reported to be affected, while weakness in these muscles is present to some degree in 60% of patients. Weakness in MG is exacerbated by exercise. While nearly all cases are reported to require chronic pharmacotherapy, results vary from good long-term control of symptoms for some patients, to significant disability accompanied by severe side effects of potent immunosuppressive therapies in many others (Gilhus and Verschuuren, Lancet Neurology 14: 1025-35 (2015)).

In the majority of cases (80%) antibodies recognising the acetylcholine receptor (AChR) are detected in patient serum. These antibodies bind to, and cause cross-linking of, AChR units at the motor end plate, the site at which stimulatory nerve endings release the neurotransmitter acetylcholine (ACh). This nerve-released ACh normally binds to AChR units of the motor end plate to trigger contraction of the underlying muscle. The presence of AChR autoantibodies causes clustering, internalisation and degradation of AChRs, thus reducing the responsiveness of the affected muscle to ACh released by the nerve, thereby causing weakness. Some MG cases without detectable AChR autoantibodies have been shown to have antibodies against one of two other proteins found at the neuromuscular junction: muscle-specific kinase (MUSK) and lipoprotein-related protein 4 (LRP4). There remains a fraction of cases (about 5%) for which no autoantibodies are detected (Binks et al. J Neurol. 263:826-34 (2016)). Thymic hyperplasia is present in some MG cases (Berrih-Aknin et al. J. Autoimmunity 52: 90-100 (2014)).

There is currently no cure for MG however, symptoms can be treated. Drugs that act by increasing the availability of ACh, in particular pyridostigmine, an inhibitor of the ACh-degrading enzyme acetylcholinesterase, is used to ameliorate symptoms of MG. However acetylcholinesterase inhibitor therapy does not adequately control symptoms of MG and patients are in need of additional treatments. That is why the therapy directed on immune system suppression is needed in order to enhance the clinical improvement. The main treatment paradigm includes steroid therapy which was proven effective but is associated with many side effects. Corticosteroid therapy has complex effects which generally include an initial transient phase of one to two weeks when symptoms can be worsened, followed by improvement due to a suppression of immune system functions. Severe symptoms may be treated with short courses of corticosteroids such as methylprednisolone delivered intravenously. Longer-term therapy with lower dose oral corticosteroids is most often used but long-term side effect risks and limited efficacy leave patients in need of further treatment options. Disease crises can also be treated by plasmapheresis, to reduce levels of autoantibodies, or intravenous immunoglobulin (IVIG) administration are used in some cases when additional therapeutic options are needed. Azathioprine is an effective drug with 2-3 mg/kg being the most optimal dose in combination with prednisolone. This combination is often recommended as a first-choice treatment for patients with generalised myasthenia gravis who need immunosuppression, and can be beneficial. However, the azathioprine effect is delayed and is practice usually seen after 6-15 months. Other treatments used by some patients or under investigation include methotrexate (an inhibitor of dihydrofolate reductase with immunosuppressant activity), rituximab (a monoclonal antibody that targets clusters of differentiation 20 expressing (CD20+) cells), eculizumab (a monoclonal antibody that binds complement protein C5) and thymectomy (Gilhus and Verschuuren, Lancet Neurology 14: 1025-35 (2015)). Despite the existence of these treatment options, patients still experience increasing and severe symptoms and accumulating disability, and there is a great need for new therapies.

Cladribine or 2-chloro-2'-deoxyadenosine has been used successfully in the oncology field with marked effects on lymphocytes. It has been found to be an effective treatment of hairy cell leukemia, chronic lymphocytic leukemia and some T cell malignancies. The addition of a chlorine atom at the 2 position of the adenine rings renders the molecule resistant to deamination by adenosine deaminase. Once taken up by cells in the body cladribine is converted enzymatically to cladribine triphosphate. Once formed inside the cell the unnatural chlorine-carrying cladribine-derived nucleotides do not easily leave the cell and they can interact with cellular enzymes that normally work on the cell's natural deoxynucleotides. Two critical enzymes influencing the levels of cladribine nucleotides within a cell are cytidine kinase (CK) and nucleotidase (NT). It has been shown that levels of CK and NT enzyme expression vary between cell types and that lymphocytes have an especially high ratio of CK to NT expression. The combination of cladribine's resistance to adenosine deaminase and lymphocytes' high CK:NT ratio leads to the concentration and retention of cladribine nucleotides in human lymphocytes. This unique situation is responsible for cladribine's selectivity towards T and B lymphocytes when administered systemically.

The accumulation of cladribine nucleotides in lymphocytes has several known deleterious effects on the survival and function of lymphocyte cells. The result of these effects is death of both dividing and non-dividing lymphocytes. As a result, it has been suggested that cladribine may be used for treating multiple sclerosis (see U.S. Pat. No. 5,506,214).

In addition to the foregoing effects of cladribine to cause death of lymphocytes by mechanisms dependent upon its intracellular phosphorylation, there are other means by which cladribine can affect immune system function. Induced cytokine production by human lymphocytes stimulated in culture by anti-CD3 and anti CD28 antibodies is decreased by cladribine treatment under conditions in which phosphorylation by CK is blocked and lymphocyte death does not occur (Laugel B. et al; *J. Neuroimmunol*; (2011); 240-241; 52-57).

Cladribine also binds with high affinity at a class of cell surface receptors called A2A (adenosine receptor class 2a). A2A receptors are found on T lymphocytes as well as other cell types in brain and the vasculature, and agents which bind A2A receptors have been shown to regulate overactive immune responses (Ohta and Sitkovsky, *Nature* 414: 916-20 (2001)).

Cladribine has been investigated as a possible treatment for some autoimmune diseases. Several studies have tested the use of cladribine in multiple sclerosis (MS) and "clinically isolated syndrome", an early condition which commonly develops into MS. Groups treated with 3.5 milligrams per kilogram body weight (3.5 mg/kg) and 5.25 mg/kg by oral tablets (approximately 200 to 400 mg cumulative dose, depending on the body weight of individual subjects) had fewer relapses, less disability, and less disease activity as visualized by magnetic resonance imaging (see Giovannoni G. et al. *NEJM* 362: 416-426 (2010), and Leist T. et al. *Lancet Neurol*. 13: 257-67(2014)). Use of cladribine has also been reported in a single patient suffering from IgM associated inflammatory peripheral neuropathy, and this intravenous administration of approximately 100 mg cumulative dose was associated with symptomatic improvement and reduced levels of pathogenic antibodies (see Ghosh A. et al.; *Neurology;* 59; 1290-1291; (2002)). There are no published reports of tests of cladribine in the treatment of MG. Therefore it has not been possible to predict the effect of cladribine treatment on myasthenia gravis Whilst cladribine has been used for treating other diseases including some leukemias and multiple sclerosis, and dosage regimens have been described (see EP 2263678) it could not have been predicted that cladribine would be effective in treating MG. The inventor has unexpectedly found that cladribine may be beneficial in the treatment or amelioration of the autoimmune neuromuscular disorder myasthenia gravis. The inventor has further unexpectedly found that the sum of cladribine's effects on the immune system allows a short period of treatment (several weeks) to provide beneficial effects on the disease for a prolonged period of over 10 months without the need for frequent retreatment. The inventor has further unexpectedly found that an autoimmune disease, and more particularly the autoimmune disease myasthenia gravis, can be treated or ameliorated by a cumulative dose of cladribine that is markedly lower than the cumulative doses that have been claimed previously to be effective in treatment or amelioration of autoimmune diseases.

SUMMARY OF THE INVENTION

According to one aspect of the invention there is provided 2-chloro-2'-deoxyadenosine, known as cladribine, or a pharmaceutically acceptable salt thereof, for use in the treatment or amelioration of myasthenia gravis.

According to a second aspect of the invention there is provided a pharmaceutical composition comprising 2-chloro-2'-deoxyadenosine, known as cladribine, for use in the treatment or amelioration of myasthenia gravis. The composition preferably comprises one or more pharmaceutically acceptable excipients.

The composition comprises from 1 milligram (mg) to 20 mg of cladribine per unit dose, preferably from 2.5 mg to 15 mg, most preferably from 8 mg to 12 mg per unit dose.

Preferably the composition is to be administered orally. For oral administration, the composition may be presented as a tablet, a capsule or a liquid formulation. It may also be presented in a liquid formulation suitable for injection.

Preferably the composition consists of cladribine or a pharmaceutically acceptable salt thereof.

According to another aspect of the invention there is provided use of 2-chloro-2'-deoxyadenosine (cladribine), or a pharmaceutically acceptable salt thereof, in the preparation of a medicament for the treatment or amelioration of myasthenia gravis.

Preferably the medicament is to be administered orally and is presented in the form of a tablet, capsule or liquid formulation.

An effective cumulative dose or amount of from 0.1 to 6 mg cladribine per kilogram of patient body weight (mg/kg) in the medicament is taken over a period of from one to two years. Preferably the effective cumulative amount comprises from 0.2 mg/kg to 2.5 mg/kg of cladribine.

According to yet another aspect of the invention there is provided a method of treating or ameliorating myasthenia gravis in a subject suffering from the disease comprising administering to the subject, or patient, a pharmaceutical composition comprising an effective amount of 2-chloro-2'-deoxyadenosine (cladribine), or a pharmaceutically acceptable salt thereof.

The composition is presented in unit dose form such as a tablet, capsule or liquid formulation for oral administration.

The pharmaceutical composition may be administered daily as a single dose.

The effective amount may be determined empirically as the effective cumulative amount of cladribine administered on between 1 and 20 dosing days, distributed over between 1 and 16 weeks, preferably between 5 and 10 weeks, that results in a reduction of CD3+ T cells of between 30 and 80%, preferably between 40 and 60% relative to pre-treatment levels.

DETAILED DESCRIPTION OF THE INVENTION

Definitions

"Amelioration" of a disease refers to the ability of a pharmaceutical composition or treatment to make the patient undertaking the treatment better or to improve the symptoms of the disease suffered by the patient or to make the disease more tolerable.

As used herein, "treating" or "treatment" means reducing, hindering the development of, controlling, alleviating and/or reversing the symptoms in an individual to which cladribine has been administered, as compared to the symptoms of an individual not being treated.

"Effective amount" of a composition refers to a composition which contains cladribine in an amount sufficient to provide a therapeutic dose over the course of treatment.

The term "unit dose" refers to physically discrete units suitable as unitary dosages for administration to patients, each such unit containing a predetermined quantity of cladribine calculated to produce the desired therapeutic effect in association with pharmaceutically acceptable ingredients.

The terms "effective cumulative amount" and "effective cumulative dose" refer to the total amount of cladribine given to a patient over time, i.e. the total dose of cladribine given in a series of treatments.

Cladribine and/or its pharmaceutically acceptable salts may be used in the practice of this invention. Suitable pharmaceutically acceptable salts refers to non-toxic acid addition salts that are generally prepared by reacting a compound with a suitable organic or inorganic acid. Examples of suitable salts include the hydrochloride, hydrobromide, sulphate, phosphate, citrate, acetate and maleate.

Cladribine may be prepared by processes well known in the art, such as those described in EP 173,059, U.S. Pat. No. 5,208,327 and Robins et al., J. Am. Chem. Soc., 106; 6379; (1984).

Whilst cladribine may be administered intravenously or subcutaneously, oral delivery is preferred for several reasons, the most important of which is patient compliance. There is also generally a cost benefit, since the cost of parenteral administration is much higher due to the necessity for the administration to be carried out by a doctor or nurse in a clinic, hospital or other specialised facility.

Oral administration of cladribine may be in capsule, tablet, oral suspension or syrup form, with capsules or tablets being preferred. Oral formulations of cladribine have been described in WO 2004/087100.

Pharmaceutical compositions of cladribine for use in the present invention may further comprise one or more pharmaceutically acceptable excipients such as alum, stabilizers, antimicrobial agents, buffers, colouring agents, flavouring agents, flavouring agents, adjuvants and the like. Where the composition is in the form of a tablet or capsule for oral administration conventional excipients, such as binding agents, fillers, lubricants, glidants, disintegrants and wetting agents may be included.

Binding agents include, but are not limited to, syrup, acacia, gelatin, sorbitol, tragacanth, mucilage of starch and polyvinylpyrrolidone. Fillers include, but are not limited to, lactose, sugar, microcrystalline cellulose, maize starch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulphate. Glidants include, but are not limited to silicon dioxide.

Tablets or pills may be provided with an enteric layer in the form of an envelope that serves to resist disintegration in the stomach and permits the active ingredients to pass intact into the duodenum or to be delayed in release. A variety of materials can be used for enteric layers or coatings, including polymeric acids or mixtures of such acids with such materials as shellac, shellac and cetyl alcohol, cellulose acetate phthalate and the like.

Compositions of this invention may also be liquid formulations including, but not limited to, aqueous or oily suspensions, solutions, emulsions, syrups, and elixers. The compositions may also be formulated as a dry product for constitution with water or other suitable vehicle before use. Such liquid preparations may contain additives including, but not limited to, suspending agents, emulsifying agents, nonaqueous vehicles and preservatives. Suspending agent include, but are not limited to, sorbitol syrup, methyl cellulose, glucose/sugar syrup, gelatin, hydroxyethylcellulose, carboxymethyl cellulose, aluminium stearate gel, and hydrogenated edible fats. Emulsifying agents include, but are not limited to, lecithin, sorbitan monooleate, and acacia. Non-aqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid.

Treatments may be given as a number of courses, each course comprising for example five consecutive days of administration of one or two tablets or capsules containing 10 mg cladribine or drinking or infusing a similar amount of cladribine in a liquid formulation on each of five days. Patients suffering from MG may, for example, receive two such courses of treatment separated by several days, for example from 21 to 30 days, at the beginning of the first treatment. This may be followed by two additional courses, also separated by from 21 to 30 days at the beginning of the second year of treatment, or only the first two courses may be used in a patient's therapy.

The total cumulative dose of cladribine over the one or two years of treatment may be from 0.1 to 6 mg/kg body weight, preferably from 0.2 to 4.0 mg/kg, most preferably 0.25 to 2.5 mg/kg per unit dose. Thus, for an 80 kg patient taking 3.5 mg/kg the total dose may be approximately 280 mg, consisting of 28 tablets containing 10 mg of cladribine each, distributed over 10 or 20 dosing days where on some days one tablet is taken whilst on others two tablets or three tablets are taken. For an 80 kg patient taking 1.0 mg/kg the total dose may be approximately 80 mg, consisting of eight tablets containing 10 mg of cladribine each, taken on eight days distributed over a period of 8 to 40 days. When administered as a liquid formulation by injection the dose regimen may be halved.

Alternatively, the baseline level of cluster of differentiation (CD)3+ T lymphocytes in a patient's blood sample is measured before the patient is given one fiveday course of treatment with a cumulative cladribine dose of 0.1 to 3.5 mg/kg. Following a period of non-treatment of from 3 to 6 weeks the lymphocyte cell numbers are re-measured. Further doses then may be administered in order to obtain a 50%±10% reduction in the numbers of CD3+ T lymphocytes.

Cladribine has been found to have a unique combination of mechanisms of action that translates into a unique profile of functional effects on autoimmunity and inflammatory mechanisms. Whilst it has mechanisms that lead to direct killing of lymphocytes with sparing of other immune and non-immune cell types, it also has an effect on lymphocytes that is independent of cytotoxic mechanisms and can affect the function of dendritic cells. Cladribine has been found unexpectedly to reduce cytokine production by induced human lymphocytes and to cause a reduction in antibody levels and disease severity effects that long outlast its presence in the body.

The invention will be further described with reference to the following examples:

Example 1

| Powder in capsule formulation | |
|---|---|
| Cladribine | 10 mg |
| Microcrystalline cellulose | 100 mg |
| Lactose | 77.8 mg |
| Croscarmellose sodium | 10 mg |
| Silicon dioxide | 0.2 mg |
| Magnesium stearate | 2 mg |
| Hard gelatin size 1 capsule shell | |

Example 2

Treatment of a Person Suffering from Myasthenia Gravis with Cladribine

A 45 year old patient with existing, acetylcholine receptor antibody positive myasthenia gravis (MG) diagnosed at age 35 years. Patient was evaluated with contrast enhanced computerised tomography scanning of his chest and no thymoma or thymic hyperplasia was found prior to treatment initiation. Treatment with steroids and pyridostigmine lasting for greater than four months had failed to control the patient's symptoms. Initiation of azathioprine treatment was tried but had to be stopped after 1 week of treatment due to severe intolerance due to nausea and vomiting. After following 3 months of observation the condition of the patient deteriorated requiring hospitalisation.

He received 20 mg cladribine, administered by subcutaneous injection of 2.5 mg cladribine in 2.5 ml in each of four limbs (total 10 mg), on each of two consecutive days. This total dose of 20 mg is markedly less than the total doses of 200-400 mg given in recent multiple sclerosis trials. Clinical assessment using two scales was performed one week before initiation of cladribine administration, and three months after first cladribine administration. The treatment with oral steroids and pyridostigmine remained stable over observation period.

The two scales used were:
Myasthenia Gravis Composite Scale (Burns T et al. Neurology 74:1434-40 (2010)
Myasthenia Gravis Activities of Daily Living (Wolfe G et al. Neurology 52: 1487-89 (1999)

Clinical Results

At three months, the patient showed a marked improvement in both the rating scales used, strongly suggesting beneficial effect of receiving cladribine (Table 1). Improved performance on the composite clinical scale (25 point improvement on the MG Composite Scale) was reflected in better performance of activities of daily living (11 point improvement on the MG Activities of Daily Living scale).

TABLE 1

Clinical Assessments of MG Patient Treated with Cladribine

| RATING SCALE | PRE-CLADRIBINE SCORE | 3 MONTHS POST-CLADRIBINE |
|---|---|---|
| MG Composite Scale | 31 | 6 |
| MG Activities of Daily Living | 19 | 8 |

The patient did not experience any adverse events that were considered by the supervising clinician to be possible side effects of receiving cladribine. In particular, cladribine did not produce a transient worsening of signs as is commonly the case with initiation of corticosteroid therapy. The clinical improvement clearly seen three months after drug administration was sustained over the following seven months, which led to gradual withdrawal of the baseline treatment.

It was the opinion of the supervising clinician that this marked, consistent and sustained improvement would have been very unlikely to have occurred without the change in treatment and that the improvement experienced by the patient was due to cladribine administration.

The invention claimed is:

1. A method of treating or ameliorating myasthenia gravis in a subject suffering from myasthenia gravis comprising administering to the subject, or patient, a pharmaceutical composition comprising an effective amount of 2-chloro-2'-deoxyadenosine (cladribine), or a pharmaceutically acceptable salt thereof.

2. The method of claim 1, wherein the cladribine or the salt thereof is administered in an effective amount determined as the effective cumulative amount of cladribine or the salt thereof administered on between 1 and 20 dosing days, distributed over between 1 and 16 weeks, that results in a reduction of CD3+ T cells of between 30 and 80%, relative to pre-treatment levels.

3. The method of claim 2, wherein the cladribine or the salt thereof is administered in an effective amount determined as the effective cumulative amount of cladribine or the salt thereof administered on between 1 and 20 dosing days, distributed over between 5 and 10 weeks, that results in a reduction of CD3+ T cells of between 40 and 60% relative to pre-treatment levels.

4. The method of claim 1, wherein the cladribine or the salt thereof is administered in an effective cumulative dose or amount of from 0.1 to 6 mg cladribine, or the salt thereof, per kilogram of patient body weight (mg/kg) and the pharmaceutical composition is taken over a period of from one to two years.

5. The method of claim 1, wherein the cladribine or the salt thereof is administered in an effective cumulative dose or amount of from 0.2 to 2.5 mg/kg cladribine or the salt thereof, per kilogram of patient body weight (mg/kg) and the pharmaceutical composition is taken over a period of from one to two years.

6. A method of treating or ameliorating myasthenia gravis in a subject suffering from myasthenia gravis comprising administering to the subject a pharmaceutical composition comprising an effective amount of 2-chloro-2'-deoxyadenosine (cladribine), or a pharmaceutically acceptable salt thereof, the cladribine or the salt thereof being administered on between 1 and 20 dosing days, distributed over between 1 and 16 weeks to treat or ameliorate said myasthenia gravis for a period of over 10 months.

* * * * *